United States Patent [19]
Moretti

[11] Patent Number: 6,114,382
[45] Date of Patent: Sep. 5, 2000

[54] METHODS FOR TREATING INFLAMMATORY BOWEL DISEASE

[76] Inventor: Itagiba G. Moretti, Rua Dep. Nilson Ribas, 1012, Londrina, Brazil, 86020-090

[21] Appl. No.: 09/189,717

[22] Filed: Nov. 11, 1998

[51] Int. Cl.⁷ .................................................... A01N 37/34
[52] U.S. Cl. ......................... 514/523; 514/525; 514/526; 514/528; 514/534; 514/538; 514/540; 514/542; 514/551; 514/613; 514/616; 514/617; 514/619; 514/620; 514/622; 514/625; 514/626; 514/628; 514/629; 514/646; 514/649; 514/651; 514/653; 514/654; 514/655; 600/562; 600/570; 600/571; 436/63; 436/174; 436/811; 435/30; 435/34; 435/40.5; 435/947
[58] Field of Search .................................... 514/523, 525, 514/526, 528, 534, 538, 540, 542, 551, 613, 616, 617, 619, 620, 622, 625, 626, 628, 629, 646, 649, 651, 653, 654, 655; 600/562, 570, 571; 436/63, 174, 811; 435/30, 34, 40.5, 947

[56] References Cited

U.S. PATENT DOCUMENTS

| | | |
|---|---|---|
| 3,143,566 | 8/1964 | Surrey . |
| 3,495,006 | 2/1970 | Wendt et al. . |
| 4,113,774 | 9/1978 | Surrey et al. . |
| 4,302,472 | 11/1981 | Cozzi et al. . |
| 4,412,992 | 11/1983 | Chan . |
| 4,455,305 | 6/1984 | Rokos . |
| 4,980,173 | 12/1990 | Halskov . |
| 5,039,703 | 8/1991 | Breuer . |
| 5,041,431 | 8/1991 | Halskov . |
| 5,292,667 | 3/1994 | Podolsky et al. . |
| 5,444,054 | 8/1995 | Garleb et al. . |
| 5,561,164 | 10/1996 | Gutteridge et al. ................ 514/682 |
| 5,604,231 | 2/1997 | Smith et al. . |
| 5,843,482 | 12/1998 | Rhodes et al. ..................... 424/653 |

OTHER PUBLICATIONS

Teclozan, Drugs of Today vol. XIV, No. 10, 1978.
Statement of Itagiba G. Moretti dated Feb. 23, 1999.

*Primary Examiner*—Frederick Krass
*Attorney, Agent, or Firm*—Woodward, Emhardt, Naughton, Moriarty & McNett

[57] ABSTRACT

The present invention provides novel compositions and methods relating to the treatment of Inflammatory Bowel Disease ("IBD"), most notably, Ulcerative Colitis, Crohn's Disease, Colitis and Diverticulitis. The invention relates to the discovery of a parasitic microsporidia infecting the epithelium cells lining the gastrointestinal tract of patients suffering from IBD. The discovery of this correlation between the disease and the microsporidia, described herein, led to the development of methods for the accurate diagnosis of patients suffering from IBD, and also of methods for treating such a patient in accordance with the invention. This discovery also provides for the development of animal models to further elucidate the mechanism of the disease and potential additional cures therefor. The present invention, in a preferred aspect, provides treatment methods wherein a patient suffering from a microsporidia infection is administered a pharmaceutically-effective amount of a N,N'-di-[halogenated-(lower alkanoyl)]-diamine compound.

33 Claims, No Drawings

METHODS FOR TREATING INFLAMMATORY BOWEL DISEASE

BACKGROUND OF THE INVENTION

1. Field of the Invention

The invention relates generally to research directed to, and medical treatment of, Inflammatory Bowel Disease ("IBD"). More specifically, the invention relates to the discovery of a correlation between IBD and an intestinal parasitic microsporidia infection. The invention therefore involves, in preferred aspects, methods for diagnosing IBD or other microsporidia infection, and methods for treating a patient, preferably a human patient, having IBD or other microsporidia infection. More particularly, the invention relates in preferred aspects to the use of pharmaceutically-active compounds for treating a patient suffering from IBD.

2. Discussion of Related Art

Inflammatory bowel disease (IBD) is a group of chronic disorders that cause inflammation and/or ulceration in the small and large intestines. Most often, IBD is classified as ulcerative colitis or Crohn's disease, but may be referred to as diverticulitis, colitis, enteritis, ileitis, and proctitis. Ulcerative colitis has also been commonly referred to as "unspecific ulcerative colitis" or "idiopathic ulcerative colitis" because physicians and scientists have been unsuccessful in their attempts to identify the etiological agent causing the disease. Ulcerative colitis causes ulceration and/or inflammation of the inner lining of the colon and rectum, while Crohn's disease is an inflammation that extends into the deeper layers of the intestinal wall. Crohn's disease may involve any segment of the digestive tract, including the mouth, esophagus, stomach, and small intestine, although characteristically the region of greatest involvement is the distal one-quarter of the small intestine and the proximal colon. Ulcerative colitis is typically isolated in the proximity of the colon. Ulcerative colitis and Crohn's disease cause similar symptoms that often resemble other conditions, such as irritable bowel syndrome (spastic colitis); therefore, the correct diagnosis may take some time, and is certainly not straightforward.

In ulcerative colitis, the inner lining of the large intestine (colon or bowel) and rectum become inflamed. The inflammation usually begins in the rectum and lower (sigmoid) intestine and spreads upward to the entire colon. Ulcerative colitis rarely affects the small intestine; however, the lower section, the ileum, is sometimes involved. The inflammation causes the colon to empty frequently, resulting in diarrhea. As cells on the surface of the lining of the colon die and slough off, ulcers (tiny open sores) form, causing pus, mucus and bleeding. Because ulcerative colitis is associated with mucosal injury, it is desirable to detect ulcerative colitis early in the patient's life, and to be able to distinguish ulcerative colitis from functional disorders such as irritable bowel syndrome. Early intervention can improve the long-range prognosis for the patient.

Ulcerative Colitis is a cosmopolitan disease estimated to affect 6 to 10 people per 10,000. There is little percentage difference among Caucasians, Blacks, and Asians, but the incidence in women is slightly higher than that in man. It occurs most often in young people ages 15 to 40, although children and older people sometimes develop the disease, these cases being rare. The above-estimated incidence rate is believed to be an underestimation of the actual number of people suffering from the disease. One reason for this belief is the difficulty in diagnosing the disease. Another reason for the possible underestimation of the number of people infected by the disease is the fact that it is not considered a reportable disease. Most patients are treated as outpatients and many statistical figures include only those patients who are periodically admitted into the hospital, reducing the real incidence statistics. Even those cases treated as outpatient, however, are very important in characterizing the morbidity and mortality of the disease. There is no doubt that treatment of IBD has become one of the most important problems of modem medicine.

Ulcerative colitis is not a new disease. Clinical descriptions that are very suggestive of ulcerative colitis can be found dating back to the Roman Empire. Until Giovanni Morgani introduced the discovery of the relationship between the symptoms of the disease and its morbid anatomical aspects, in 1761, the diagnostic conclusions lacked scientific backing. In the Nineteenth Century, the golden century for medicine, difficulties existed in the efforts to distinguish ulcerative colitis from infectious or parasitic dysentery. Even so, in 1865, during the American Civil War, there were descriptions of probable cases of ulcerative colitis. The superficial inflammation of the mucosa, especially the crypts/follicles was pointed out and, according to medical officials of the time, this feature contributed to the differentiation between ulcerative colitis and infectious dysentery. More credit has been given, however, to Wilks & Moxon, who in 1875, published the first edition of the book "Lectures and Pathological Anatomy." Even though they did not mention unspecific ulcerative colitis in the first edition, they described and defined what they called "simple ulcerative colitis" in the chapter "The Inflammations of the Large Intestine." The data that was reported referred to post-mortem macroscopical findings.

One of the most significant contributions to the knowledge about unspecific ulcerative colitis was the work of Hale-White, contemporary to Wilks, published in 1888. This author described 29 cases of inflammatory intestinal lesions. A more in-depth analysis of his findings leads us to possible cases of ulcerative colitis (including neoplasm and toxic megacolon), Crohn's disease (involving small intestine and colon), tuberculosis, typhoid fever, lymphoma, ischemia, appendicitis, and uraemic colitis. Hale-White, in 1895, published a new article entitled "Colitis," clarifying to the medical community the concept of non-infectious ulcerative colitis. Finally, with the advent of a procedure termed rectosigmoidoscopy, and also contrasted radiological colon tests, starting in the Twentieth Century, the study of unspecific ulcerative colitis was directed to those patients still living. Until then the descriptions and conclusions were based only on post-mortem data.

Ulcerative colitis evolves in varied patterns. Typically, the disease is progressive, characterized by episodes of exacerbation and remission. Generally, the clinical course is more severe when the disease first appears early in the patient's life. The prognosis is poorer when the extent of the involvement is greater, and is generally more favorable when only the sigmoid colon and the rectum are involved. There are instances of fulminating initial symptoms and others in which the symptoms are initially weak but later become severe. There may be huge variations in the intermediary phases as to the diarrhea, sometimes accompanied by mucous, mucous and blood, or mucous-blood and pus (which is characterized as bio-mucous-sanguinolent). There are cases in which the daily episodes of diarrhea may reach 30, but those are exceptions. Generally, when the severity of the disease is considered to be medium to high, the number of daily episodes is between four and 10.

While the most common symptoms of ulcerative colitis are abdominal pain and bloody diarrhea, patients also may suffer fatigue, weight loss, loss of appetite, rectal bleeding, and loss of body fluids and nutrients. Severe bleeding can also lead to anemia, and patients sometimes also develop skin lesions, joint pain, inflammation of the eyes, or liver disorders. To date, no reason has been substantiated for the link between colitis and these problems outside the bowel. Scientists think these complications may occur when the immune system triggers inflammation in other parts of the body. These disorders are usually mild and go away when the symptoms of colitis are treated.

Because the etiological agent causing IBD has for so long remained undetermined, diagnosis of, for example, ulcerative colitis and Crohn's disease has been very problematic and its cure has remained elusive, except through surgical removal of the colon. Medical treatment has historically been directed toward simply treating the symptoms of the disease, thereby decreasing the number, frequency and severity of acute exacerbations of IBD and preventing secondary complications. At best, however, the results have been disappointing. With respect to the difficulty of diagnosing the disease, only in recent years has the diagnosis been done by the most correct and widely acceptable method, rectosigmoidoscopy. This procedure, which typically utilizes a videocolonscope, is a useful way to diagnose the intestinal alterations associated with ulcerative rectum colitis, colitis, diverticulitis and Crohn's disease, because it provides visualization of the intestinal mucous. Videocolonoscopy is commonly followed by a biopsy, allowing the physician to further observe a site of inflammation. The typical characteristics of the lesions may then be identified by their morphophysiological characteristics, thereby allowing the physician to reach a conclusion as to the specific condition. Given that this is a technique not readily accessible to lower income patients, however, there are speculations that there are many misdiagnosed cases that are taken as simple viral infections, or even bacterial diarrhea, masking the real numbers of cases.

Although much scientific evidence shows that people with ulcerative colitis have abnormalities of the immune system, doctors have not been able to determine conclusively whether these abnormalities are a cause or result of the disease. A number of studies have suggested that components of the immune system may mediate or contribute to injury observed in the colonic mucosa, but it remains unclear what initiates the pathogenic processes. It has been suggested that a primary abnormality of the immune system and its regulation might serve as primary initiating factors, or that the disease process might be initiated by an infectious agent and the injury then perpetuated through immune-mediated or other processes. One leading theory has suggested that some agent, possibly a virus or an atypical bacterium, interacts with the body's immune system to trigger an inflammatory reaction in the intestinal wall. Although the mucosal injury observed during episodes of acute disease can resemble the effects of any of a number of recognized infectious agents, no transmissible infectious agent was consistently identified with ulcerative colitis. Alternatively, it has been suggested that aberrant structures in the colonic mucosa might increase susceptibility of the colonic mucosa to a lumen factor, predisposing the colonic mucosa to injury by causing a defect in the mucosal barrier or initiating inappropriate activation of injurious immune-mediated processes.

About half of patients have only mild symptoms. Others suffer frequent fever, bloody diarrhea, nausea, and severe abdominal cramps. Only in rare cases, when complications occur, is the disease fatal. There may be remissions, periods when the symptoms go away, that last for months or even years. However, most patients' symptoms eventually return. This changing pattern of the disease can make it hard for the doctor to tell when treatment has helped.

Ulcerative colitis has historically been thought to be untreatable and incurable and a patient with the disease must learn to live with it and use, for indefinite periods, medication that is meant to control it, such as, for example, *sulfanilamide*, 5ASA, and *corticoids*, which provide only palliative activity. Patients with either mild or severe colitis are usually treated with sulfasalazine, which can be used for as long as needed; however, side effects such as nausea, vomiting, weight loss, heartburn, diarrhea, and headache occur in some cases. Patients who do not do well on sulfasalazine often react well to related drugs known as 5-ASA agents. In some cases, patients with severe disease, or those who cannot take sulfasalazine-type drugs are given adrenal steroids (drugs that help control inflammation and affect the immune system) such as prednisone or hydrocortisone. All of these drugs can be used in oral, enema, or suppository forms. Additionally, other drugs may be given to relax the patient or to relieve pain, diarrhea, or infection; however, corticosteroids and sulfasalazine are the only drugs that have been shown to shorten an acute attack of ulcerative colitis. (Truelove, S. C., Witts, L. J., *Cortisone in ulcerative colitis and the indications for colectomy*. World J. Surg. 1988; 12:142–7). Corticosteroids achieve a rapid remission more frequently than sulfasalazine; however, the combination of these agents is widely used for treatment of colitis attacks (Truelove, S. C., Witts, L. J., *Cortisone in ulcerative colitis and the indications for colectomy*. World J. Surg. 1988; 12:142–7).

Patients with ulcerative colitis occasionally have symptoms severe enough to require hospitalization. In these cases, the doctor will try to correct malnutrition and to stop diarrhea and loss of blood, fluids, and mineral salts. To accomplish this, the patient may need a special diet, feeding through a vein, medications, or sometimes, surgery.

The risk of colon cancer is greater than normal in patients with widespread ulcerative colitis. The risk may be as high as 32 times the normal rate in patients whose entire colon is involved, especially if the colitis exists for many years. The most severe and alarming form of ulcerative colitis is the kind in which the symptoms persist for 15 years or longer. The percentage of these cases that evolve into colon cancer surpasses 17%.

About 20 to 25% of ulcerative colitis patients eventually require surgery for removal of the colon because of massive bleeding, chronic debilitating illness, perforation of the colon, or risk of cancer. Sometimes the doctor will recommend removing the colon when other medical treatment fails or when the side effects of steroids or other drugs threaten the patient's health. The most common surgery is the proctocolectomy, the removal of the entire colon and rectum, with ileostomy, creation of a small opening in the abdominal wall where the tip of the lower small intestine, the ileum, is brought to the skin's surface to allow drainage of waste. The opening (stoma) is about the size of a quarter and is usually located in the right lower corner of the abdomen in the area of the beltline. A pouch is worn over the opening to collect waste and the patient empties the pouch periodically.

Proctocolectomy with continent ileostomy is an alternative to the standard ileostomy. In this operation, the surgeon creates a pouch out of the ileum inside the wall of the lower abdomen. The patient is able to empty the pouch by inserting a tube through a small leak-proof opening in his or her side. Creation of this natural valve eliminates the need for an external appliance. However, the patient must wear an external pouch for the first few months after the operation.

Sometimes an operation that avoids the use of a pouch can be performed. In an ileoanal anastomosis ("pull-through operation"), the diseased portion of the colon is removed and the outer muscles of the rectum are preserved. The surgeon attaches the ileum inside the rectum, forming a pouch, or reservoir, that holds the waste. This allows the patient to pass waste through the anus in a normal manner, although the bowel movements may be more frequent and watery than usual.

In view of the above background, there is a great need in the field of medicine for a method of treating patients suffering from IBD, wherein the treatment avoids the need for highly invasive and life-altering surgical procedures, is directed to the disease itself, and does not merely treat the symptoms. Further, there is a great need in the art for a method whereby a patient may be screened in the first instance for the disease, thereby reducing the risk of misdiagnosis and resulting ineffective treatments. The present invention satisfies these and other needs in the field of treating IBD.

SUMMARY OF THE INVENTION

The present invention relates to the discovery that the presence of pathologies identified as inflammatory bowel disease ("IBD") are substantially correlated with the presence of a microsporidia infection in a patient's gastrointestinal tract. An additional discovery featured in the present invention is that a gastrointestinal microsporidia infection may be eradicated or substantially eradicated by administering to a patient suffering therefrom an appropriate amount of N,N'-di-[halogenated-(lower alkanoyl)]-diamine compound, and that the eradication of the infection results in the amelioration of IBD.

In one aspect of the invention, there is provided a method for the treatment of a patient suffering from inflammatory bowel disease. The method includes (1) providing a composition including a compound toxic to microsporidia present in the gastrointestinal tract of a patient suffering from inflammatory bowel disease; and (2) administering to the patient an amount of the composition effective to kill substantially all living microsporidia from the patient's gastrointestinal tract.

In another aspect of the invention, there is provided a method for the treatment of a gastrointestinal microsporidia infection. The method includes administering to a patient suffering from said infection a composition comprising an effective amount of Teclozan. It is preferred that the Teclozan be orally administered in three treatment series spaced apart by from about 6 to about 18 days, and that each treatment series include orally administering from about 2000 mg to about 4000 mg Teclozan to the patient on a first day; orally administering from about 1000 mg to about 3000 mg Teclozan to the patient on a second day; orally administering from about 1000 mg to about 3000 mg Teclozan to the patient on a third day; and orally administering from about 1000 mg to about 3000 mg Teclozan to the patient on a fourth day. The first through fourth days are preferably consecutive days.

In an alternate aspect, the present invention provides an oral dosage form of Teclozan for administration to a patient suffering from an inflammatory bowel disease. The oral dosage form preferably comprises at least about 800 mg Teclozan.

In another aspect of the invention, there is provided a method for killing a microsporidia, comprising contacting the microsporidia with an amount of Teclozan that is toxic to the microsporidia, thereby killing the microsporidia.

The invention also provides a method for screening a patient for inflammatory bowel disease, comprising (1) examining a member selected from the group consisting of a feces sample from a patient, an intestinal biopsy sample from the patient and an in situ portion of the patient's intestine for the presence of a microsporidia cell or a mature microsporidia spore; and (2) determining the existence of inflammatory bowel disease based upon the presence or absence of the microsporidia cell or mature microsporidia spore.

In another aspect of the invention, there is provided a method for making a non-human animal featuring a pathology substantially resembling inflammatory bowel disease. This method includes (1) providing a non-human animal and a spore from a microsporidium that is pathogenic to the animal; and (2) introducing the spore into the animal's gastrointestinal tract such that the spore infects one or more of the animal's epithelium cells; wherein the microsporidium initiates a pathology in the animal substantially resembling inflammatory bowel disease.

It is an object of the invention to provide compositions and methods whereby patients suffering from IBD or other microsporidia infection may be treated to ameliorate the disease or infection without the necessity of highly invasive and life-altering surgical procedures.

It is also an object of the invention to provide methods whereby patients suffering from symptoms characteristic of IBD may be quickly and effectively diagnosed so that it may be determined whether the practice of the invention is desirable or whether the patient is suffering from an unrelated disease or condition such as, for example, irritable bowel syndrome or amoebic dysentery.

Another object of the invention is to provide methods whereby further research and development of treatments of IBD may be readily conducted using an animal model comprising an animal that features a microsporidia-induced pathology resembling IBD.

Further objects, advantages and features of the present invention will be apparent from the detailed description herein.

DETAILED DESCRIPTION OF THE INVENTION

For the purposes of promoting an understanding of the principles of the invention, reference will now be made to a preferred embodiment and specific language will be used to describe the same. It will nevertheless be understood that no limitation of the scope of the invention is thereby intended, such alterations and further modifications in the described embodiment, and such further applications of the principles of the invention as described herein being contemplated as would normally occur to one skilled in the art to which the invention relates.

The present invention in one aspect provides a treatment for inflammatory bowel disease ("IBD"), which disease primarily exists in two forms, namely, ulcerative colitis and Crohn's disease. IBD has plagued a significant portion of mankind for many years. The invention relates to the discovery that patients examined by the inventor who were found to be suffering from IBD were also found to harbor a parasitic microsporidia infection; the discovery that eradication or substantial eradication of the infection results in the amelioration of IBD; and the further discovery of an excellent manner of eradicating or substantially eradicating such an infection. While it is not intended that the invention be limited to any theory whereby it achieves its advantageous result, it is believed that the present inventor has identified the etiological agent that causes, aggravates or facilitates IBD, namely, a parasitic microsporidium that is pathogenic to mankind.

A microsporidium is an organism belonging to the phylum Microsporos. Phylum Microsporos is known to include a plurality of genres pathogenic for mankind, such as, for example, Nosema (*N. connon; N. comeun; N. ocularum*), Pleitophora, Encephalitozoon (*E. cuniculi; E. hellen; E. intestinalis*), Enterocytozoan (*E bieneusi*) and Septata (*S. intestinalis*). A variety of genres are also known to be pathogenic for non-human animals. It is believed that the shape of a Microsporidia spore is related to the pathology and/or transmittal of the disease.

While the pre-application work by the present inventor has focused upon the genres of Microsporidia pathogenic to mankind, it is expected that alternative aspects of the invention may be used to eradicate a wide variety of Microsporidia from non-human animals as well. Thus, the discovery of the association between Microsporidia infection and IBD, and the corresponding discovery of methods for advantageously eradicating or substantially eradicating the infection, are all features of the present invention that enable the effective treatment of a wide variety of Microsporidia infections. The term "microsporidium" is used herein to designate an organism, belonging to the phylum Microsporos, which is pathogenic to humans or, in a broader aspect of the invention, to other animals.

Microsporidia are commonly described as primitive eukaryotic, obligate, intracellular protozoan pathogens, and have been reported to cause opportunistic infections in AIDS patients. While it is known that microsporidia are occasionally present in AIDS patients, microsporidia were not, prior to the present invention, linked to IBD, nor has there been developed a satisfactory treatment for microsporidia infections in AIDS patients. One treatment that has been used for AIDS patients is Albendazole, an anti-parasitic drug; however, this drug has not proven to effectively and consistently eradicate microsporidia from a patient being treated therewith. The drug Metronidazole can also be helpful and has elicited a slight response in some patients; however, this medication does not decrease the population of infectants. Thus, the symptoms only decrease their intensity temporarily, and no effective cure takes place. Other drugs that have been used to treat microsporidia infections include Azitromicina, Quinacrina, Paranomicina and Octreotide; however, none have proven successful.

Microsporidia are believed to reproduce by gradually releasing spores into the gastrointestinal ("GI") tract from within the epithelium cells. The release of spores by the epithelium cells has been observed to be repetitive and unpredictable in nature. It is understood that most of the spores released into the GI tract will ultimately be passed from the GI tract as waste. The generally understood mechanism of how a microsporidia infection is transmitted from person to person (or animal to animal) is that mature spores passed from one individual are then ingested by another. As these mature spores reach a new host's digestive tract, they initiate a complex process of fixation in the organ and begin anew with the reproductive process. It is believed that ingested spores release sporazoites, which then primarily infect the cells lining the GI tract of the new host. The organisms undergo asexual reproduction which allows many enterocytes (epithelium cells) to be infected in the new host even if no additional spores are ingested. Infected enterocytes die and are shed into the GI tract allowing the spores to be excreted in the stool, thus continuing the life cycle of the microsporidia. It is believed that some of the released spores may become fixed in the infected individual's GI tract before being eliminated, thereby spreading the extent of infection and the severity of the disease in the infected individual.

It is also believed that, if the infection remains at low levels in a host, the host may remain healthy, but be a potential source of transmission of the infection to other individuals. While the invention is not intended to be limited by the above description of the microsporidia life cycle, the present inventor has established that the presence of microsporidia within the gastrointestinal epithelium cells, and the resulting presence of spores within the GI tract, are positive indicators of IBD or the imminent onset of IBD. Similarly, the inventor has found that patients suffering from IBD, after undergoing treatment in accordance with the invention, have no microsporidia, or a substantially reduced number of microsporidia, in their epithelium cells and have no spores, or a substantially reduced umber of spores, within their GI tracts. In the experimental work conducted by the present inventor, many individuals positively identified to suffer from IBD, including at least about 40 individuals in 1998 were examined, and in 100% of the individuals, IBD has been successfully ameliorated, without any recorded relapse or side effect, in accordance with the invention. In an advantageous aspect, therefore, the invention features the discovery that a patient suffering from IBD may be advantageously treated by destroying the microsporidia population in the infected person's GI tract.

A compound which may advantageously be used in accordance with the invention to eradicate or substantially eradicate microsporidia from a patient in accordance with the invention is a compound that has a toxic effect on the microsporidia, and which is suitable to be administered to a patient (human or non-human animal) without significant detrimental side effects (referred to herein as "the compound"). The present inventor's discovery of the correlation between IBD and microsporidia infection enables the effective treatment of the disease in accordance with the invention by killing the parasite.

The microsporidia infection is preferably eliminated or substantially eliminated in accordance with the invention by contacting the site of infection with a N,N'-di-[halogenated-(lower alkanoyl)]-diamine compound. The term "lower" as used herein in connection with, for example, an alkanoyl, an alkylene, an alkyl, an alkenyl or an alkynyl, is intended to designate a carbon chain, either straight chain or branched chain, that includes from about 1 to about 6 carbons. A preferred compound for the practice of the invention, therefore, is a N,N'-di-[halogenated-(lower alkanoyl)]-diamine compound. In one preferred aspect of the invention, the N,N'-di-[halogenated-(lower alkanoyl)]-diamine compound has the general structural formula I:

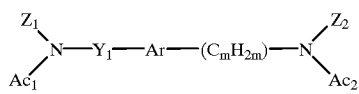

where $Y_1$ is lower-alkylene; m is a number from 0 to 6 inclusive and $C_mH_{2m}$ represents lower-alkylene when m is from 1 to 6; Ar is a lower-divalent-aromatic radical; $Ac_1$ and $Ac_2$ each are halogenated (lower-alkanoyl); and $Z_1$ and $Z_2$ are members selected from the group consisting of hydrocarbon radicals of the formula R, hydroxyalkyl radicals of the formula —Y$_2$—OH, hydrocarbonoxyalkyl radicals of the formula —Y$_2$—O—R, acyloxyalkyl radicals of the formula —Y$_2$O—Ac', cyanoalkyl radicals of the formula —Y$_2$—CN and carbamylalkyl radicals of the formula —Y$_2$—CONH$_2$, where Y$_2$ is alkylene having from two to six carbon atoms and having its two free valence bonds on different carbon atoms, R is hydrocarbon radical having from one to eight carbon atoms and Ac' is carboxylic-acyl having from one to eight carbon atoms.

In another preferred aspect of the invention, the N,N'-di-[halogenated-(lower-alkanoyl)]-diamine compound has the general structural formula II:

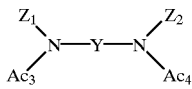

where Y is selected from the group consisting of

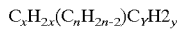

and alkylene having from two to sixteen carbon atoms, wherein said alkylene can be interrupted by members selected from the group consisting of O, S, SO, SO$_2$, NH, N(lower-alkyl), N(lower-alkenyl), N(lower-alkynyl), N-[halogenated-(lower-alkanoyl)], CH=CH and C≡C, where x and y each are numbers from 0 to 6 inclusive and n is an integer from 3 to 8 inclusive, C$_x$H$_{2x}$ and C$_y$H$_{2y}$ each representing lower-alkylene when x and y each are from 1 to 6 and C$_n$H$_{2n-2}$ representing cycloalkylene; Ac$_3$ and Ac$_4$ each are halogenated-(lower-alkanoyl) having from two to three halogen atoms; and Z$_1$ and Z$_2$ are members selected from the group consisting of hydrocarbon radicals of the formula R, hydroxyalkyl radicals of the formula —Y$_2$—OH, hydrocarbonoxyalkyl radicals of the formula —Y$_2$O—R, acyloxyalkyl radicals of the formula —Y$_2$—O—Ac', cyanoalkyl radicals of the formula —Y$_2$—CN and carbamylalkyl radicals of the formula —Y$_2$—CONH$_2$ where Y$_2$ is alkylene having from two to six carbon atoms and having its two free valence bonds on different carbon atoms, R is a hydrocarbon radical having from one to eight carbon atoms and Ac' is carboxylic-acyl having from one to eight carbon atoms.

More preferably, the compound selected for use in accordance with the invention is a N,N'-bis(dichloroacetyl) diamine, and the most preferred compound presently known is N,N'-bis-(dichloroacetyl)-N,N'-bis(2-ethoxyethyl)-1,4-xylylenediamine, commonly known as, and hereinafter referred to as, Teclozan. N,N'-di-[halogenated-(lower alkanoyl)]-diamine compounds, and methods for making the same, are more fully described in U.S. Pat. No. 3,143,566 to Surrey, which is incorporated herein by reference in its entirety. Prior to the present invention, however, it was not known that compounds described herein could be advantageously used in accordance with the invention to treat a patient suffering from the very serious, and commonly life altering disease, IBD. Teclozan, or N,N'-bis(dichloroacetyl)-N,N'-bis(2-ethoxyethyl)-1,4-xylylene diamine, is represented by the structural formula:

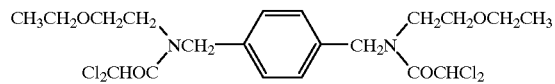

Teclozan is the most potent analog of a series of bis (dichloroacetyl) diamines that have previously been shown to possess activity against *E. histolytica* in vitro and in intestinal amebiasis. Animal studies have shown that Teclozan has little to no toxicity. The oral LD$_{50}$ in mice is greater than 8000 mg/Kg and administration of doses as high as 480 mg/Kg to rats and 2500 mg/Kg to monkeys during a six-month period did not produce abnormal results in any of the animals. It is believed that Teclozan is practically atoxic because of minimal absorption. Symptoms of meteorism and flatulence are rare and, if a consequence of medication, may be relieved by the administration of an antispasmodic (such as, for example, belladonna tincture) or an adsorbent (such as, for example, Kaolin). Symptoms of nausea and vomiting are rare and seldom require cessation of medication. Teclozan is commercially available in pharmaceutical form, and is manufactured by Winthrop Product, Inc., a division of Sterling Drug, Inc. (New York, N.Y., USA), under the trade name FALMONOX®. FALMONOX® is a drug for treatment of patients suffering from intestinal amebiasis (amoebic dysentery) and also has been described, along with other N,N'-di-[halogenated-(lower alkanoyl)]-diamine compounds, as exhibiting gonadal hormone potentiating effects and antispermatogenic activity. Prior to the present invention, however, there was no known link between the compound and the advantageous effects described herein relating to treatment of IBD or other microsporidial infection.

The present invention provides, in one preferred aspect, a method for treating a patient suffering from IBD (e.g., colitis, ulcerative colitis, diverticulitis or Crohn's disease) or other condition caused by an intestinal microsporidium infection. This method includes administering to the patient a compound toxic to the microsporidium, in an amount effective to kill substantially all of the microsporidia present in the patient. In a preferred aspect of the invention, the compound is a N,N'-di-[halogenated-(lower alkanoyl)]-diamine compound. More preferably, the compound is a bis(dichloroacetyl-diamine compound, and most preferably the compound is Teclozan. It is, of course, preferred to first establish that a patient's condition is indeed IBD, and not another disease having related symptoms, such as, for example, irritable bowel syndrome, prior to administering the compound to the patient.

The compound may preferably be combined with a pharmaceutically acceptable carrier in a ratio that enables efficient delivery of an effective dose of the compound to a patient. In a certain preferred aspect of the invention the compound is administered to the patient orally. Because IBD affects a patient's GI tract, oral administration is preferred to ensure that the compound is contacted with the protozoa irrespective of the exact intestinal location of the infection. It is understood by a skilled artisan that microsporidia may also infect a patient's kidneys, lungs, eyes and other organs. When such an infection is identified, it is contemplated that such an infection may preferably be eradicated in accordance with the invention using an alternate manner of delivery. For example, where a patient's eyes are infected by microsporidia, it may be preferred to deliver the compound via an aqueous solution or suspension, such as in a conventional saline administered in the form of eyedrops. Alternatively, where a patient's lungs are infected by microsporidia, it may be preferred to deliver the compound via a gaseous suspension, such as a conventional inhaler. It is contemplated that, in treating certain forms of microsporidia infection, a compound selected in accordance with the invention may desirably be chemically altered to make its inoculation more efficient, such as, for example, by increasing its absorption properties. While the above and other alternate delivery mechanisms are contemplated by the invention, it is understood that IBD patients are preferably treated by oral administration of the compound.

In a preferred aspect of the invention, a patient is administered a composition comprising an effective amount of the compound, optionally in admixture with an orally administrable pharmaceutically-acceptable carrier. In a preferred embodiment, the carrier is selected whereby the compound is released therefrom after the composition reaches the patient's colon. Such a carrier may be selected, for example, in accordance with the teachings of U.S. Pat. No. 4,980,173 to Halskov, which is hereby incorporated by reference herein is its entirety. The controlled release may preferably be dependent upon the prevailing pH in the colon. In an alternative embodiment, the compound is released from the carrier after the composition reaches the patient's small intestine, and preferably the compound is released gradually throughout the small intestine and continuously throughout the colon of the patient. Another alternative method of delivering the compound which may be used to advantageously deliver the compound to the site of infection, is by enema.

The selection of a proper oral dosage for a given patient is dependent upon the amount of the compound necessary to provide an effective concentration of the compound at the site of infection. It is understood, therefore, that a variety of factors are involved in determining a proper dosage, including but not limited to the size of the patient, the degree to which the compound may be altered by passage through the digestive system, and the severity of the infection. While a preferred embodiment of the invention is described with respect to delivery of Teclozan to an adult human patient, it is understood that preferred dosages to a child or smaller, non-human animal, and preferred dosages of alternative compounds may differ so that a substantially equivalent effective concentration of the compound is achieved at the site of infection.

In a preferred manner of treating an adult human patient with Teclozan in accordance with the invention, from about 5,000 mg to about 13,000 mg of Teclozan is orally administered to the patient during a treatment series spanning a time period of from about 3 to about 5 days. It is more preferred that the amount administered during a first portion of this series be greater than the amount administered during a second portion. For example, where the patient is treated for a series of four days, it is preferred that from about 2500 mg to about 3500 mg of Teclozan be administered to the patient during the first day and that from about 1500 mg to about 2500 mg be administered to the patient during the second, third and fourth days of the four-day treatment series. It is believed that one treatment series, such as the one described herein, effectively kills all, or substantially all, living microsporidia in the GI tract.

In one preferred manner of treating a patient, a plurality of doses of Teclozan are administered to the patient during the treatment series, each dose being separated in time by from about 4 to about 12 hours. Preferably, at least one high dose is followed by at least one moderate dose. It is preferred that a high dose comprise at least about 1000 mg of Teclozan, more preferably from about 1000 to about 3000 mg of Teclozan, and most preferably from about 1500 to about 3000 mg. It is preferred that a moderate dose comprise at least about 500 mg of Teclozan, more preferably from about 500 to about 2000 mg of Teclozan, and most preferably from about 500 to about 1500 mg. It is again noted that the total amount of Teclozan administered in the plurality of doses is preferably from about 5000 to about 13000 mg, more preferably from about 6000 to about 12,000 mg.

It is also preferred that the first treatment series be followed by one or more additional treatment series, each one preferably beginning from about 6 to about 18 days, more preferably from about 8 to about 18 days, and most preferably from about 10 to about 15 days, following the beginning of the previous treatment series. It is preferred that about 3 or 4 additional treatment series be administered. The additional treatment series are preferably administered to the patient in substantially the same manner as the first treatment series, although a variety of follow-up treatment schedules may be employed in accordance with the invention. While it is not intended that the present invention be limited by any theory by which it achieves its advantageous result, the administration of additional treatment series is preferred in inventive methods because it is believed that mature spores of the intracellular parasite are present in the GI tract even after the first treatment series is completed. Therefore, in the absence of subsequent treatment series, there remains the possibility that mature spores, previously released by the microsporidia and still residing within the patient's Gl tract, will re-infect the patient, thereby impairing the effectiveness of an inventive treatment.

In a preferred manner of treating a patient suffering from a microsporidia infection, the patient is treated with three or four series of Teclozan doses, with a total administration of about 9000 mg of Teclozan per series. Each series is preferably spaced apart by about 15 days, with the following schedule for each series:

| | | |
|---|---|---|
| Day 1 | 1000 mg, three times per day | --3000 mg total |
| Day 2 | 1000 mg, two times per day | --2000 mg total |
| Day 3 | 1000 mg, two times per day | --2000 mg total |
| Day 4 | 1000 mg, two times per day | --2000 mg total |
| Total treatment for series: | | --9000 mg |

This manner of treatment has proven effective to rid an adult human patient of a microsporidia infection and, advantageously, to prevent recurrence of IBD in a patient suffering from the disease.

In another aspect of the invention, there is provided a method for screening a patient suffering from diarrhea, rectal bleeding, weight loss, abdominal cramping and/or abdominal pain for the presence of IBD. In this aspect of the invention, a feces sample or an intestinal biopsy sample may be collected from the patient and examined for the presence of microsporidia cells and/or mature microsporidia spores. Alternatively, the presence of microsporidia cells and/or microspores may be identified using colonoscopy procedures. Thus, the present invention provides not only methods for treating IBD patients, but also methods for reliably diagnosing patients suffering from one or more of the above-noted symptoms for IBD. This is a very valuable tool for physicians and other health care providers because a wide variety of medical conditions feature very similar symptoms and diagnosis of the cause of the symptoms is often quite challenging.

In yet another aspect, the present invention provides methods for making an animal model that may be advantageously used, for example, to test the effects of various treatments on IBD. A significant amount of resources have been invested in the study of IBD, and a major limitation in investigating the pathogenic mechanisms responsible for the mucosal injury observed during chronic inflammation of the intestine and colon has been the relative paucity of relevant animal models. Two models of colitis produced in rats that have received attention are the acetic acid and trinitrobenzene sulfonic acid (TNBS) models.

The mechanism by which acetic acid produces the diffuse colitis is thought to involve non-specific, acid induced injury to the colonic mucosa that is followed by an acute inflammatory response. Apparently, the protonated form of the acid is required to induce the colitis since neither HCl (pH 2.3) nor sodium acetate (pH 7.0) is effective in eliciting the inflammatory response. However, there is some evidence to suggest that acetic acid may promote other pathophysiological events (e.g. fluid and electrolyte secretion) using non-cytotoxic concentrations of the acid.

More recent studies have demonstrated that the intrarectal administration of the hapten, TNBS, in the presence of a mucosal barrier breaker such as ethanol, produces an acute and possibly chronic colitis in unsensitized rats. The mechanism(s) by which buffered or unbuffered TNBS in the presence of ethanol initiates inflammation of in unsensitized animals is unclear; however, it has been suggested to involve macrophage-mediated recognition and lysis of TNBS-modified autologous cells within the mucosa. However, more recent evidence suggest more complicated mechanisms. For example, the barrier breaker, ethanol, is an extremely potent pro-inflammatory solvent alone. Furthermore, it has been demonstrated that TNBS is metabolized by certain colonic enzymes and substrates to yield both pro-inflammatory and cytotoxic oxidants that could initiate colonic inflammation. Grisham et al., "Metabolism of Trinitrobenzene Sulfonic Acid by the Rat Colon Produces Reactive Oxygen Species," GASTROENTEROLOGY, Vol. 101, pages 540–547 (1991).

A recent study directly compared the acetic acid and the TNBS (+ETOH) models of colitis and found that either model may be useful to study those events that occur at the time of inflammation (e.g. arachidonate metabolism, granulocyte infiltration and metabolism, etc.) or during repair. However, the use of these models of colitis may have significant limitations in understanding those immunological events that initiate the acute and chronic inflammatory episodes. For example, the inflammation and tissue injury observed in human inflammatory bowel disease is most probably a results of inappropriate immunological activation (e.g. autoimmune, infectious agent, etc.) whereas the inflammation induced by the intrarectal application of acetic acid, ethanol or ethanol plus TNBS is a response to extensive mucosal injury. Thus, the mechanisms by which inflammation (and mucosal injury) are achieved in the human disease have been postulated to be very different than those in the experimental models.

Another model of acute and chronic distal colitis in rats has been described in which purified bacterial cell wall polymers (derived from Group A streptococci) are injected into the distal colon of genetically-susceptible rats. Sartor et al., Granulomatous Entercolitis Induced by Purified Bacterial Cell Wall Fragments," GASTROENTEROLOGY, Vol. 89, pages 587–595 (1985). This model produces an acute and chronic inflammation characterized by the infiltration of large numbers of inflammatory cells, enhanced mucosal permeability, interstitial fibrosis, and mucosal thickening as well as the extraintestinal manifestations of arthritis, hepatic and splenic granulomas. Unlike most models of colitis, the inflammation induced in this model promotes mucosal and submucosal injury rather than the injury causing the inflammation.

In view of the above, there is an absence in the art of a satisfactory animal model for IBD. The present invention provides an excellent animal model for the study of IBD. It is believed, based upon pre-application work, that the present inventor has identified the etiological agent that causes IBD, namely, microsporidia. Therefore, the invention provides methods whereby a non-human animal, preferably a rodent, such as, for example, a mouse, is caused to harbor within its epithelium cells a living microsporidia parasite pathogenic to the animal. An animal model thus made is expected to exhibit a pathology substantially resembling IBD. By "substantially resembling" is meant that the pathology features intestinal lesions having characteristics analogous to lesions present in a human suffering from, for example, ulcerative colitis, colitis, diverticulitis or Crohn's disease. It is expected that such an animal model may be made by introducing a spore of a microsporidium pathogenic to the animal into the animal's colon and/or small intestine. The spore is preferably introduced, for example, by causing the animal to ingest one or more mature microsporidia spores that effect such a pathology. It is believed that such an animal model may be advantageously used in further study of IBD and for the potential development of additional treatments therefor.

While the invention has been described in detail in the foregoing description, the same is to be considered as illustrative and not restrictive in character, it being understood that only the preferred embodiments have been described and that all changes and modifications that come within the spirit of the invention are desired to be protected.

What is claimed is:

1. A method for the treatment of a patient suffering from inflammatory bowel disease, comprising:

selecting a patient based upon a diagnosis of inflammatory bowel disease;

providing a composition including a compound toxic to microsporidia present in the gastrointestinal tract of the patient; and responding to the diagnosis by administering to the patient an amount of the composition effective to kill living microsporidia in the patient's gastrointestinal tract.

2. The method in accordance with claim 1, wherein the inflammatory bowel disease is selected from the group consisting of colitis, ulcerative colitis, diverticulitis and Crohn's disease.

3. The method in accordance with claim 1, wherein the compound is a N,N'-di-[halogenated-(lower alkanoyl)]-diamine derivative.

4. The method in accordance with claim 1, wherein the compound is a N,N'-bis-(dichloroacetyl) diamine.

5. The method in accordance with claim 1, wherein the compound is Teclozan.

6. The method in accordance with claim 1, wherein the composition is administered to the patient orally.

7. The method in accordance with claim 6, wherein the composition is orally administered to the patient over a first time period of from about 3 to about 5 days.

8. The method in accordance with claim 6, wherein the composition comprises Teclozan, and wherein from about 5,000 to about 13,000 mg of Teclozan is orally administered to the patient over the course of about 3 to about 5 days.

9. The method in accordance with claim 6, wherein said oral administering is achieved in a first series of four consecutive days, the method comprising:

first administering from about 2500 to about 3500 mg of Teclozan to the patient in the first day; and next administering from about 1500 to about 2500 mg of Teclozan to the patient in each of the second, third and fourth days.

10. The method in accordance with claim 9, wherein a second series is administered to the patient in substantially the same manner as the first series, and wherein the second series begins from about 6 to about 18 days after the first day.

11. The method in accordance with claim 10, wherein a third series is administered to the patient in substantially the same manner as the first series or the second series, and wherein the third series is begun from about 6 to about 18 days after the second series begins.

12. The method in accordance with claim 11, wherein a fourth series is administered to the patient in substantially the same manner as the first series, the second series or the third series, and wherein the fourth series is begun from about 6 to about 18 days after the third series begins.

13. The method in accordance with claim 1, wherein said administering comprises introducing the composition into the gastrointestinal environment such that the compound is present in the gastrointestinal environment in an amount effective to prevent the survival and reproduction of the microsporidia present in the patient's gastrointestinal tract.

14. The method in accordance with claim 1, further comprising, before said providing, identifying the presence of a microsporidia in the gastrointestinal tract, wherein the amount administered is an amount whereby the compound is contacted with the microsporidia at a concentration toxic to the microsporidia.

15. The method in accordance with claim 14, wherein said administering comprises orally administering the composition.

16. The method in accordance with claim 14, wherein said administering comprises orally administering to the patient a therapeutically effective amount of an oral dosage form of the composition adapted to release the compound in the gastrointestinal tract of the animal and being capable of killing substantially all living microsporidia present in the animal's gastrointestinal tract.

17. The method in accordance with claim 16, wherein the therapeutically effective amount of the composition is estimated on the basis of the body weight of the subject and the severity of the parasite infection.

18. The method in accordance with claim 14, wherein said administering comprises introducing a plurality of doses of the composition into the gastrointestinal tract over a prescribed period of time to eradicate the microsporidia and spores produced thereby from the gastrointestinal tract.

19. The method in accordance with claim 18, wherein the plurality of doses comprises at least one dose comprising at least about 1000 mg of the compound, followed by at least one dose comprising at least about 500 mg of the compound.

20. The method in accordance with claim 18, wherein the plurality of doses comprises at least one high dose, comprising from about 1000 mg to about 3000 mg of the compound, followed by at least one moderate dose comprising from about 500 mg to about 2000 mg of the compound; wherein each dose is separated by a period of time of from about 4 to about 12 hours.

21. The method in accordance with claim 20, wherein the high doses comprise from about 1500 mg to about 3000 mg of Teclozan, and wherein the moderate dose comprises from about 500 to about 1500 mg of Teclozan.

22. The method in accordance with claim 1, wherein the composition comprises the compound in admixture with an orally administrable pharmaceutically-acceptable carrier.

23. The method in accordance with claim 22, wherein the compound is released from the carrier essentially after the composition reaches the patient's colon.

24. The method in accordance with claim 23, wherein the delayed release is dependent upon the prevailing pH in the colon.

25. The method in accordance with claim 22, wherein the compound is released from the carrier gradually throughout the small intestine and continuously throughout the colon of the patient.

26. The method in accordance with claim 22, wherein the compound is released from the carrier essentially after the composition reaches the patient's small intestine.

27. A method for the treatment of a gastrointestinal microsporidia infection, comprising administering to a patient suffering from said infection a composition comprising an effective amount of Teclozan;

wherein said administering comprises orally administering the Teclozan in three treatment series spaced apart by from about 6 to about 18 days;

wherein each treatment series comprises orally administering from about 2000 mg to about 4000 mg Teclozan to the patient on a first day; orally administering from about 1000 mg to about 3000 mg Teclozan to the patient on a second day; orally administering from about 1000 mg to about 3000 mg Teclozan to the patient on a third day; and orally administering from about 1000 mg to about 3000 mg Teclozan to the patient on a fourth day; and wherein the first through fourth days are consecutive days.

28. An oral dosage form of Teclozan for administration to a patient suffering from an inflammatory bowel disease, comprising at least about 800 mg Teclozan.

29. A method for killing a microsporidia, comprising:

contacting the microsporidia with an amount of Teclozan that is toxic to the microsporidia, thereby killing the microsporidia.

30. A method for screening a patient for inflammatory bowel disease, comprising:

examining a member selected from the group consisting of a feces sample from a patient, an intestinal biopsy sample from the patient and an in situ portion of the patient's intestine for the presence of a microsporidia cell or a mature microsporidia spore; and determining the existence of inflammatory bowel disease based upon the presence or absence of the microsporidia cell or mature microsporidia spore.

31. A method for making a non-human animal featuring a pathology substantially resembling inflammatory bowel disease, comprising:

providing a non-human animal and a spore from a microsporidium that is pathogenic to the animal; and introducing the spore into the animal's gastrointestinal tract such that the spore infects one or more of the animal's epithelium cells;

wherein the microsporidium initiates a pathology in the animal substantially resembling inflammatory bowel disease.

32. The method in accordance with claim 31, wherein the animal is a rodent.

33. The method in accordance with claim 31, wherein the animal is a mouse.

* * * * *